US008258360B2

(12) United States Patent
Clark et al.

(10) Patent No.: US 8,258,360 B2
(45) Date of Patent: Sep. 4, 2012

(54) MULTIPHASE ALKYLAROMATICS PRODUCTION

(75) Inventors: Michael C. Clark, Chantilly, VA (US); Vijay Nanda, Houston, TX (US); Brian Maerz, Chelmsford, MA (US)

(73) Assignees: ExxonMobil Chemical Patents Inc., Houston, TX (US); Stone & Webster, Inc., Houston, TX (US)

( * ) Notice: Subject to any disclaimer, the term of this patent is extended or adjusted under 35 U.S.C. 154(b) by 779 days.

(21) Appl. No.: 11/885,819

(22) PCT Filed: Mar. 1, 2006

(86) PCT No.: PCT/US2006/007261
§ 371 (c)(1),
(2), (4) Date: May 13, 2008

(87) PCT Pub. No.: WO2006/107470
PCT Pub. Date: Oct. 12, 2006

(65) Prior Publication Data
US 2008/0242907 A1    Oct. 2, 2008

Related U.S. Application Data

(60) Provisional application No. 60/666,874, filed on Mar. 31, 2005.

(51) Int. Cl.
*C07C 2/66*    (2006.01)
*C07C 6/12*    (2006.01)
(52) U.S. Cl. ......... 585/467; 585/449; 585/475; 585/323
(58) Field of Classification Search .................. 585/467, 585/449, 475, 323
See application file for complete search history.

(56) References Cited

U.S. PATENT DOCUMENTS

| 3,631,122 | A | 12/1971 | Berger |
| 3,751,504 | A | 8/1973 | Keown et al. |
| 3,751,506 | A | 8/1973 | Burress |
| 3,755,483 | A | 8/1973 | Burress |
| 4,891,458 | A | 1/1990 | Innes et al. |
| 4,992,606 | A | 2/1991 | Kushnerick et al. |
| 5,105,041 | A | 4/1992 | Ferk et al. |
| 5,149,894 | A | 9/1992 | Holtermann et al. |
| 5,258,565 | A | 11/1993 | Kresge et al. |
| 5,371,310 | A | 12/1994 | Bennett et al. |
| 5,453,554 | A | 9/1995 | Cheng et al. |
| 5,476,978 | A | 12/1995 | Smith, Jr. et al. |
| 5,998,687 | A | 12/1999 | Woodle et al. |
| 6,002,058 | A * | 12/1999 | Hearn et al. .................. 585/448 |
| 6,077,498 | A | 6/2000 | Diaz Cabanas et al. |
| 6,252,126 | B1 | 6/2001 | Netzer |
| 6,995,295 | B2 | 2/2006 | Clark et al. |

(Continued)

FOREIGN PATENT DOCUMENTS
EP    0 432 814    6/1991
(Continued)

*Primary Examiner* — Thuan Dinh Dang
(74) *Attorney, Agent, or Firm* — Roberts Mlotkowski Safran & Cole, P.C.

(57) ABSTRACT

A process for producing a monoalkylated aromatic product in a reactor by reacting a mixed phase mixture of an alkylatable aromatic compound feedstock with another feedstock comprising alkene component in a reaction zone containing an alkylation catalyst. An effluent comprising the monoalkylated aromatic product and polyalkylated aromatic compounds exits from the reaction zone in liquid phase. The polyalkylated aromatic compounds can be separated as feed stream for transalkylation reaction in a transalkylation reaction zone.

23 Claims, 1 Drawing Sheet

U.S. PATENT DOCUMENTS

| | | |
|---|---|---|
| 2002/0128529 A1 | 9/2002 | Chen |
| 2004/0059167 A1 | 3/2004 | Clark et al. |
| 2004/0171899 A1 | 9/2004 | Pohl |

FOREIGN PATENT DOCUMENTS

| | | |
|---|---|---|
| EP | 0 629 549 | 12/1994 |
| EP | 0 949 227 | 10/1999 |
| WO | 97/17290 | 5/1997 |
| WO | 00/39253 | 7/2000 |
| WO | 01/21562 | 3/2001 |
| WO | 2004/026797 | 4/2004 |

\* cited by examiner

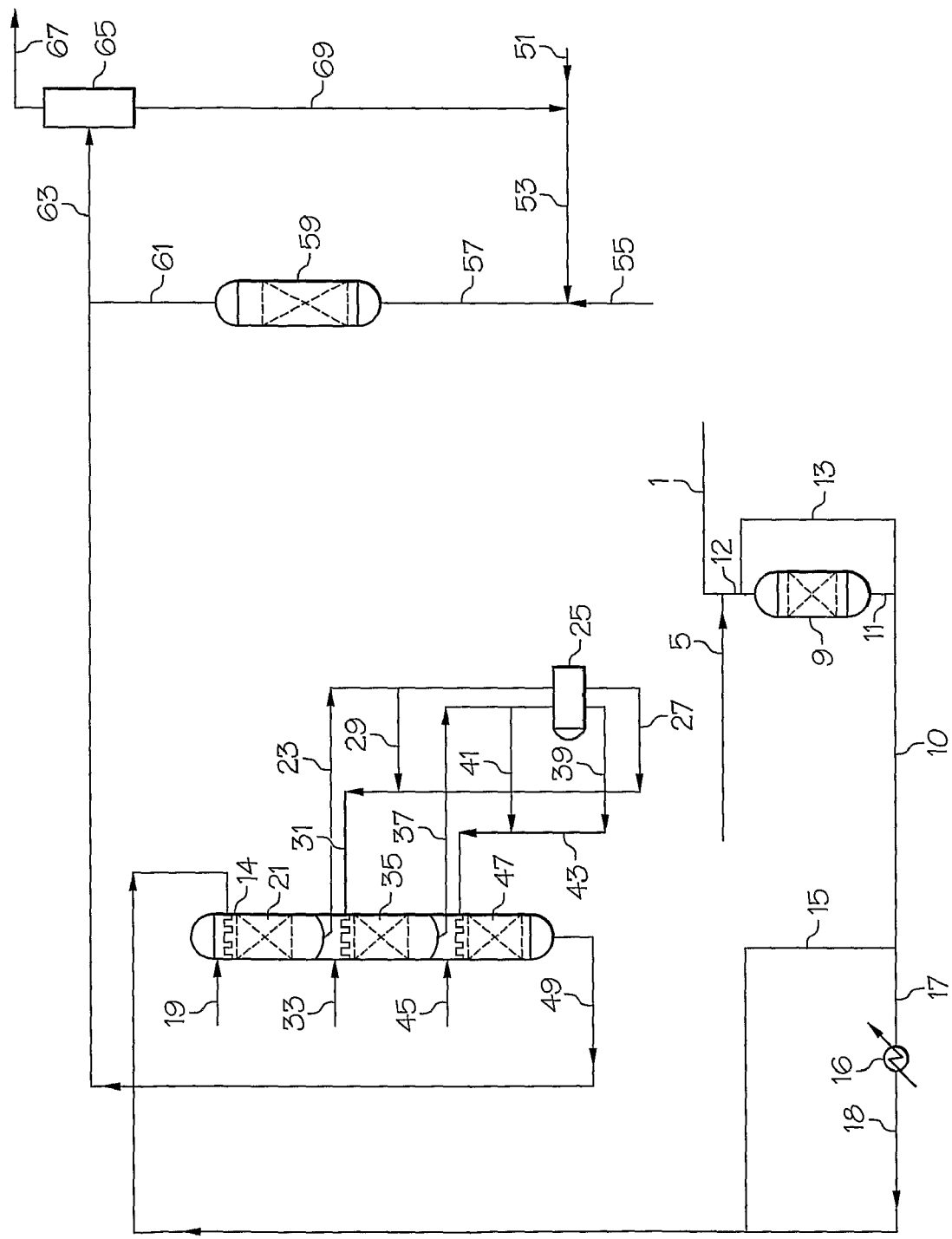

MULTIPHASE ALKYLAROMATICS PRODUCTION

CROSS REFERENCE TO RELATED APPLICATIONS

This application is a 35 U.S.C. 371 National Stage Application of International Application No. PCT/US2006/007261, filed Mar. 1, 2006, which claims the benefit of Provisional Application No. 60/666,874, filed Mar. 31, 2005, the disclosures of which are hereby incorporated by reference in their entireties.

FIELD

The present invention relates to a process for producing monoalkylated aromatic products, particularly ethylbenzene and cumene.

BACKGROUND

Ethylbenzene is a key raw material in the production of styrene and is produced by the reaction of ethylene and benzene in the presence of an acid alkylation catalyst. Older ethylbenzene production plants, those typically built before 1980, used $AlCl_3$ or $BF_3$ as the acidic alkylation catalyst. Plants built after 1980 have in general used zeolite-based acidic catalysts as the alkylation catalyst.

Commercial ethylbenzene manufacturing processes typically require the use of concentrate ethylene that has a purity exceeding 80 mol. %. For example, a polymer grade ethylene has a purity exceeding 99 mol. % ethylene. However, the purification of ethylene streams to attain chemical or polymer grade is a costly process and hence there is considerable interest in developing processes that can operate with lower grade or dilute ethylene streams. One source of a dilute ethylene stream is the off gas from the fluidized bed catalytic cracking or steam-cracking units of a petroleum refinery. The dilute ethylene stream from such units, after removal of reactive impurities, such as propylene, typically contains about 10-80 mol. % ethylene, with the remainder being ethane, hydrogen, methane, and/or benzene.

Three types of ethylation reactor systems are used for producing ethylbenzene, namely, vapor phase reactor systems, liquid phase reactor systems, and mixed phase reactor systems.

In vapor-phase reactor systems, the ethylation reaction of benzene and ethylene is carried out at a temperature of about 350 to 450° C. and a pressure of 690-3534 KPa-a (6-35 $kg/cm^2$-g) in multiple fixed beds of zeolite catalyst. Ethylene exothermically reacts with benzene in the presence of such zeolite catalyst to form ethylbenzene. About 10-30 mol. % of the ethylbenzene formed further reacts with ethylene to form di-ethylbenzene isomers (DEB), tri-ethylbenzene isomers (TEB) and heavier aromatic products (heavies). These undesirable reaction products, namely DEBs, TEBs and heavies, are often collectively referred to as polyethylated benzenes (PEBs).

By way of example, vapor phase ethylation of benzene over a catalyst comprising crystalline aluminosilicate zeolite ZSM-5 is disclosed in U.S. Pat. Nos. 3,751,504 (Keown et al.), 3,751,506 (Burress), and 3,755,483 (Burress).

In most cases, vapor phase ethylation systems use polymer grade ethylene feeds. Moreover, although commercial vapor phase processes employing dilute ethylene feeds have been built and are currently in operation, the investment costs associated with these processes is high.

In recent years the trend in industry has been to shift away from vapor phase ethylbenzene reactors in favor of liquid phase reactors. Liquid phase reactors operate at a temperature of about 150-280° C., which is below the critical temperature of benzene (290° C.). The rate of the ethylation reaction in a liquid phase reaction is lower as compared to a comparable vapor phase reaction. Hence, the catalyst volumes required for the liquid phase reaction are greater than those for the liquid phase reaction, but the lower design temperature of the liquid phase reaction economically compensates for the negatives associated with the higher catalyst volume.

Liquid phase ethylation of benzene using a catalyst comprising zeolite beta is disclosed in U.S. Pat. No. 4,891,458 and European Patent Publication Nos. 0432814 and 0629549. More recently it has been disclosed that MCM-22 and its structural analogues have utility in these alkylation/transalkylation reactions, for example, U.S. Pat. No. 4,992,606 (MCM-22), U.S. Pat. No. 5,258,565 (MCM-36), U.S. Pat. No. 5,371,310 (MCM-49), U.S. Pat. No. 5,453,554 (MCM-56), U.S. Pat. No. 5,149,894 (SSZ-25); U.S. Pat. No. 6,077,498 (ITQ-1); International Patent Publication Nos. WO97/17290 and WO01/21562 (ITQ-2).

Commercial liquid phase ethylbenzene plants normally employ polymer grade ethylene. Moreover, although plants can be designed to accept ethylene streams containing up to 30 mol. % ethane by increasing the operating pressure, the costs associated with the design and operation of these plants have proven to be significant.

Technology has also been developed for the production of ethylbenzene in a mixed phase using reactive distillation. Such a process is described in U.S. Pat. No. 5,476,978. In mixed phase processes the ethylene stream and benzene streams form a mixed phase and may employ dilute ethylene streams since the ethylation reaction temperature is below the dew point temperature of the dilute ethylene/benzene mixture, but above the bubble point temperature. The diluents of such dilute ethylene feed, namely ethane, methane and hydrogen, remain essentially in the vapor phase. The benzene in the reactor is distributed between the vapor phase and the liquid phase, and the ethylbenzene and PEB reaction products remain essentially in the liquid phase.

U.S. Pat. No. 6,252,126 discloses a mixed phase process for producing ethylbenzene by reaction of a dilute ethylene stream containing 3 to 50 mol. % ethylene with a benzene stream containing 75 to 100 wt. % benzene. The reaction is conducted in an isothermal ethylation section of a reactor, which also includes a benzene stripping section, where the unreacted benzene is thermally stripped from the ethylation products. Integrated, countercurrent vapor and liquid traffic is maintained between the ethylation section and the benzene stripping section.

U.S. patent application Ser. No. 10/252,767 discloses a process for the production of ethylbenzene by reacting benzene with a dilute ethylene stream containing 20 to 80 wt. % ethylene and ethane. The reaction takes place in one of a series of series-connected reaction zones in the presence of an alkylation catalyst comprising a molecular sieve such as MCM-22. The temperature and pressure of the reaction zone are maintained such that the benzene and dilute ethylene feedstock are under liquid phase conditions. The intermediate products between reaction zones are cooled. A portion of alkane, e.g., ethane, in the intermediate products are removed to maintain liquid phase conditions by avoiding accumulation of ethane from zone to zone.

The present invention provides a new alkylation process where the feedstocks are in mixed phase (partially vapor and partially liquid) and the product stream is in liquid phase.

There is a phase transfer from mixed phase to liquid in any portion of the alkylation reaction zone. One advantage of this invention is the lower cost to maintain feedstocks in mixed phase other than liquid phase. Another advantage of this invention is the low temperature of liquid phase alkylation.

SUMMARY OF THE INVENTION

In an embodiment, the present invention relates to a process for producing an alkylated aromatic product in a reaction zone comprising the steps of:
(a) feeding a predominantly liquid phase first feedstock which comprises alkylatable aromatic compound(s) and an at least partially vapor phase second feedstock which comprises at least one alkene compound, to the reaction zone, wherein the reaction zone is operated under conditions sufficient to ensure that the mixture of the first feedstock and the second feedstock is in mixed phase in at least a portion of the reaction zone; and
(b) contacting the feedstock mixture and an alkylation catalyst in the reaction zone, to produce a first effluent, which comprises the alkylated aromatic product, wherein the first effluent exits the reaction zone in predominantly liquid phase.

In another embodiment, the process relates to a process for producing a monoalkylated aromatic product, the process comprising the steps of:
(a) feeding a predominantly liquid phase first feedstock which comprises alkylatable aromatic compound(s) and an at least partially vapor phase second feedstock which comprises at least one alkene compound, to a reaction zone, wherein the reaction zone is operated under conditions to maintain the mixture of the first feedstock and the second feedstock in mixed phase in at least a portion of the reaction zone;
(b) contacting the feedstock mixture and an alkylation catalyst in the reaction zone, to produce a first effluent which comprises the monoalkylated aromatic product and polyalkylated aromatic compounds, wherein the first effluent exits the reaction zone in a predominantly liquid phase;
(c) contacting the polyalkylated aromatic compounds and a third feedstock, which comprises alkylatable aromatic compound(s) in the presence of a transalkylation catalyst in a transalkylation reaction zone under transalkylation conditions, to produce a second effluent, which comprises monoalkylated aromatic product.

In another embodiment, the process further comprises the step of separating the first and second effluents to recover the monoalkylated aromatic product. In another preferred embodiment, the process further comprises the step of separating the first effluent to recover the polyalkylated aromatic compounds. In another embodiment, the process comprises the step of contacting the transalkylation feedstock and a third feedstock that comprises alkylatable aromatic compounds in the presence of a transalkylation catalyst in a transalkylation reaction zone under transalkylation conditions to produce a second effluent which comprises additional monoalkylated aromatic product.

In another embodiment, this invention relates to a process for producing an alkylaromatic compound in a multistage reactor having at least two reaction zones, the process comprising the steps of: (a) feeding a predominantly liquid phase first feedstock which comprises alkylatable aromatic compound(s) and an at least partially vapor phase second feedstock which comprises at least one alkene compound to a first reaction zone, wherein the first reaction zone is operated under conditions sufficient to ensure the mixture of the first feedstock and the second feedstock in mixed phase in at least a portion of the first reaction zone; (b) contacting the feedstock mixture and a first alkylation catalyst in the first reaction zone, to produce a first effluent which comprises the monoalkylated aromatic compound and polyalkylated aromatic compounds, wherein the first effluent is in a liquid phase upon exit of the first reaction zone; (c) cooling the first effluent stream to form a cooled first effluent stream; (d) feeding at least a portion of the cooled first effluent stream and a third feedstock to a second reaction zone of the multistage reactor operated under second conditions, wherein the third feedstock comprises alkylatable aromatic compound(s); and (e) contacting the mixture of step (d) with a second alkylation catalyst in the second reaction zone to produce a second effluent which comprises the monoalkylated aromatic product.

In another embodiment, the process further comprises the step of (f) separating the first and second effluents to recover the monoalkylated aromatic product. In another embodiment, the process comprises the step of (g) further separating the first and second effluents to recover the polyalkylated aromatic compounds as a transalkylation feedstock; and (h) contacting the transalkylation feedstock with a fourth feedstock which comprises alkylatable aromatic compound(s) in the presence of a transalkylation catalyst in a transalkylation reaction zone under transalkylation conditions, to produce a third effluent which comprises monoalkylated aromatic product. In another embodiment, the process may further comprise the step of (i) separating the third effluent, to recover the monoalkylated aromatic product.

In the embodiments of the present invention, the process is suitable for retrofitting an existing ethylbenzene or cumene plant having a vapor, liquid, or mixed phase alkylation reactor. In another embodiment of this invention, the above mentioned processes are suitable for retrofitting an existing $AlCl_3$ or $BF_3$ ethylbenzene or cumene plant.

In the embodiments of the present invention, the first feedstock has at least 98 wt. % liquid phase, preferably, at least 99 wt. % liquid phase. In yet another aspect of each of the above embodiments, the first effluent has at least 98 wt. % liquid phase, preferably, at least 99 wt. % liquid phase.

In the embodiments of the present invention, a suitable alkylation catalyst comprises a molecular sieve selected from the group consisting of MCM-22, MCM-36, MCM-49 and MCM-56, beta zeolite, faujasite, mordenite, PSH-3, SSZ-25, ERB-1, ITQ-1, ITQ-2, zeolite Y, Ultrastable Y (USY), Dealuminized Y (DealY), rare earth exchanged Y (REY), ZSM-3, ZSM-4, ZSM-18, ZSM-20, and any combination thereof. The transalkylation catalyst in such embodiments comprises a molecular sieve selected from the group consisting of MCM-22, MCM-36, MCM-49 and MCM-56, beta zeolite, faujasite, mordenite, PSH-3, SSZ-25, ERB-1, ITQ-1, ITQ-2, zeolite Y, Ultrastable Y (USY), Dealuminized Y (DealY), rare earth exchanged Y (REY), ZSM-3, ZSM-4, ZSM-18, ZSM-20, and any combination thereof.

In the embodiments of the present invention, the conditions of the reaction zone(s) include a temperature of 100 to 285° C. (212 to 500° F.) and a pressure of 689 to 4601 kPa-a (100 to 667 psia).

In the embodiments of the present invention, the second feedstock comprises at least 10 mol. % alkene, preferably, the second feedstock comprises at least 50 mol. % alkene, more preferably, the second feedstock comprises at least 80 mol. % alkene, even more preferably, the second feedstock comprises at least 90 mol. % alkene. In another embodiment, the second feedstock is a concentrate ethylene or propylene. In another embodiment, the second feedstock is a mixture of concentrate ethylene feedstock(s) or propylene feedstock(s) and a dilute ethylene feedstock(s) or propylene feedstock(s). In another embodiment, the second feedstock is a dilute ethylene or propylene only.

In another one embodiment, the monoalkylated aromatic product comprises ethylbenzene, the first feedstock comprises benzene, second feedstock comprises a mixture of ethylene, methane, and ethane, the polyalkylated aromatic compounds comprises a mixture of di-ethylbenzene and tri-ethylbenzene.

In another embodiment, the monoalkylated aromatic product comprises cumene, the first feedstock comprises benzene, second feedstock comprises a mixture of propylene, propane, methane, and ethane, the polyalkylated aromatic compounds comprises a mixture of di-isopropylbenzene and tri-isopropylbenzene.

In the embodiments of the present invention, the transalkylation conditions include a temperature of 100 to 450° C. (212 to 842° F.) and a pressure of 689 to 4601 kPa-a (100 to 667 psia).

DESCRIPTION OF THE DRAWINGS

FIG. 1 is a flow diagram of a process for producing ethylbenzene in accordance with an embodiment of the present invention.

DETAILED DESCRIPTION OF THE PREFERRED EMBODIMENTS

Detail Description of the Process

Referring to FIG. 1, a reactor 14 is shown having at least three series-connected reaction zones, namely reaction zone 21, reaction zone 35, and reaction zone 47. At least a portion of a first feedstock 1 that is predominately in the liquid phase and comprises an alkylatable aromatic compound is fed to a by-passable reactive guard bed 9 having a reaction zone. A second feedstock 5 that is at least partially vapor phase and comprises an alkene and an alkene and an alkane is also fed to the by-passable reactive guard bed 9. The portion of first feedstock 1 and second feedstock 5 are combined as mixed feedstock 12. Alternatively, a portion of said mixed feedstock 12 may be by-passed around the by-passable reactive guard bed 9 as a by-pass stream 13. At least a portion of said mixed feedstock 12 is supplied to a reaction zone of the reactive guard bed 9. The reaction zone of reactive guard bed 9 comprises at least one suitable alkylation catalyst (as defined below), including but not limited to MCM-22, MCM-36, MCM-49, MCM-56, and combinations thereof. At least a portion of said mixed feedstock 12 is contacted with a suitable alkylation catalyst under suitable alkylation conditions in the reaction zone to produce a first effluent 11 that exits the reaction zone in the liquid phase. First effluent 11 is then combined with the by-pass stream 13 as a combined effluene. First effluent 11 is comprised of an alkylated aromatic compounds (e.g., ethylbenzene or cumene), any unreacted alkene (e.g., ethylene), unreacted alkylatable aromatic compounds (e.g., benzene), and non-reactive light diluents (e.g., hydrogen, nitrogen, methane, and ethane). The combined effluent 10 is then cooled in heat exchanger 16 and then supplied as stream 18 to an inlet portion of first reaction zone 21 of alkylator 14. A portion of the combined stream 10 may by-pass the heat exchanger 16 via line 15.

As shown in FIG. 1, stream 19 flows co-currently with streams 18, or stream 15 if heat exchanger 16 is bypassed, through first reaction zone 21 of alkylator 14. Similarly, stream 33 flows co-currently with stream 27, or stream 29 if heat exchanger 25 is bypassed, through second reaction zone 35 of alkylator 14 and stream 45 flows co-currently with stream 43, or stream 4 if heat exchanger 25 is bypassed, through third reaction zone 47 of alkylator 14.

At least a portion of stream 17 comprised of unreacted alkylatable aromatic compound is alkylated with the alkene in the second feedstock 19 in the presence of the suitable alkylation catalyst to produce additional alkylated aromatic product that is at least predominately liquid phase. The reaction zone of reactive guard bed 9 may be operated at suitable alkylation conditions at or near 100% alkene conversion. Alternatively, such reaction zone may be operated at lower alkene conversions that may produce a first effluent 11 comprised of reduced amounts of such alkylated aromatic compounds and increased amounts of unreacted alkene and unreacted alkylatable aromatic compounds as compared to the amounts obtained at higher conversions. An at least partially vapor phase second feedstock 19 comprised of at least one alkene compound(s) is also fed to first reaction zone 21. At least a portion of the reaction zone is operated under conditions of temperature and/or pressure that are sufficient to ensure that the mixed feedstock 15 and/or 18, and second feedstock 19 are maintained in a mixed phase. Such mixed-base may change to liquid phase at any point of the reaction zone 21 due to the alkylation of the aromatic compound with alkene to form the alkylated aromatic compound. The reaction zone 21 comprises at least one suitable alkylation catalyst (as defined below), including, but not limited to MCM-22, MCM-36, MCM-49, MCM-56 and combinations thereof. Mixed feedstock 15 and second feedstock 19 are contacted in the presence of the suitable alkylation catalyst in reaction zone 21 to produce a first effluent 23 which comprises an alkylated aromatic product. Reaction zone 21 is maintained under conditions such that first effluent 23 exits said zone in predominantly liquid phase.

Any of the reaction zones of alkylator 14 may be operated at suitable alkylation conditions at or near 100% alkene conversion. Alternatively, one of such reaction zone may be operated at lower alkene conversions that may produce an effluent comprised of reduced amounts of such alkylated aromatic compounds and increased amounts of unreacted alkene and unreacted alkylatable aromatic compounds as compared to the amounts obtained at higher conversions.

First effluent 23 from the reaction zone 21 is passed to heat exchanger 25 to form cooled first effluent 31 that is supplied to reaction zone 35. A portion of the first effluent 23 from the reaction zone 21 may-pass the heat exchanger 25 via line 29. Additional second feedstock 33, comprised of at least one alkene, is fed to the reaction zone 35.

Cooled first effluent 31 and additional second feedstock 33 are contacting with a second suitable alkylation catalyst (as listed above) under suitable alkylation conditions to produce a second effluent 37. Second effluent 37 may be in the liquid phase or mixed phase and is comprised of additional alkylated aromatic product and is passed to heat exchanger 25 where it is cooled to form cooled effluent 43 that is supplied to reaction zone 47. Again, a portion of the second effluent 43 from the reaction zone 35 may by-pass the heat exchanger 25 via line 41.

Cooled second effluent 43 and additional third feedstock 45 (as defined below) are contacting with a third suitable alkylation catalyst (as listed above) under suitable alkylation conditions to produce a third effluent 49.

Third effluent 49 from he reaction zone 47, which may be in the liquid phase or mixed phase, is comprised of the desired monoalkylated aromatic product as well as any unreacted alkene, unreacted alkylatable aromatic compound and small quantities of polyalkylated aromatic compounds, methane, ethane and other impurities.

At least a portion of third effluent 49 may be supplied to separation block 65 in which the polyalkylated aromatic compounds (PEBs) are separated to form PEB stream 69. PEB stream 69, and optionally additional polyalkylated aromatic compounds stream 51, are combined to form transalkylator feedstock 57. Transalkylator feedstock 57 and additional first feedstock 55 (as defined below) are contacted in the presence of a suitable transalkylation catalyst (as defined below) in one or more transalkylators 59, to produce transalkylator effluent 61 that is comprised of additional alkylated aromatic compounds. At least a portion of transalkylator effluent 61 may be in the liquid phase or the vapor phase.

Transalkylator 59 is operated under conditions such that 20-100 wt. %, preferably 40 to 80 wt. %, of the polyalkylated aromatic compounds are converted to monoalkylated aromatic compound. Transalkylator effluent 61 from transalkylator 59 may be supplied to separation block 65. Optionally, transalkylator effluent 61 may be combined with third effluent 49 from the alkylator 18 and then supplied to the separation block 65. The desired alkylated aromatic compound (e.g., ethylbenzene or cumene) is separated as product stream 67.

Although one heat exchanger 25 is shown in the FIG. 1, the scope of the invention is not so limited and the scope of invention envisions one or more multiple heat exchangers. Such heat exchanger, for example, may be used as a means to generate steam to preheat the feed, e.g., feed to the transalkylation reactor, and heat integration with other plant streams. At least a portion of at least one of the reaction zones in the alkylator and/or reactive guard bed, may be operated in a mixed-phase. Other such reaction zones may be operated in the vapor phase mode, a liquid phase, a mixed phase, or a combined mixed-phase and/or liquid phase mode.

Feedstocks

The first feedstock comprises an alkylatable aromatic compound. The first feedstock is predominately liquid phase. The term "aromatic" in reference to the alkylatable compounds, which are useful herein, is to be understood in accordance with its art-recognized scope which includes alkyl substituted and unsubstituted mono- and polynuclear compounds. Compounds of an aromatic character, which possess a heteroatom, are also useful provided they do not act as catalyst poisons under the reaction conditions selected.

Substituted aromatic compounds, which can be alkylated herein, must possess at least one hydrogen atom directly bonded to the aromatic nucleus. The aromatic rings can be substituted with one or more alkyl, aryl, alkaryl, alkoxy, aryloxy, cycloalkyl, halide, and/or other groups, which do not interfere with the alkylation reaction.

Suitable aromatic hydrocarbons include benzene, naphthalene, anthracene, naphthacene, perylene, coronene, and phenanthrene, with benzene being preferred.

Suitable alkyl substituted aromatic compounds include toluene, xylene, isopropylbenzene, normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethyl anthracene; 2-methyl anthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate containing substantial quantities of benzene, toluene and/or xylene constitutes a particularly useful feed for the alkylation process of this invention. Although the process is particularly directed to the production of ethylbenzene from polymer grade and dilute ethylene, it is equally applicable to the production of other $C_7$-$C_{20}$ alkylaromatic compounds, such as cumene, as well as $C_6$+ alkylaromatics, such as $C_8$-$C_{16}$ linear and near linear alkylbenzenes.

The second feedstock comprises an alkene compound. Typically, the second feedstock includes a concentrated alkene feedstock, e.g., polymer grade alkene, and a dilute alkene feedstock, e.g., catalytic cracking off-gas.

The concentrated alkene alkylating agent of the feedstock useful in the process of this invention includes an alkene feed comprised of at least 80 mol. % of the alkene and preferably at least 99 mol. % to 100 mol. %.

The dilute alkylating agent of the feedstock useful in the process of this invention includes a dilute alkene feed which contains at least one alkene and optionally at least one alkane. For example, where the alkene is ethylene, the alkane may be ethane and/or methane. Other components, such as hydrogen, may also exist in the dilute alkylating agent. Typically, the dilute alkene feed comprises at least 10 mol. % of the alkene, preferably from 20 to 80 mol. % of the alkene. One particularly useful feed is the dilute ethylene stream obtained as an off gas from the fluid catalytic cracking unit of a petroleum refinery.

In one embodiment of the invention, the second feedstock includes a concentrated alkene feedstock only. In another embodiment of the invention, the second feedstock includes a dilute alkene feedstock only. In yet another embodiment of the invention, the second feedstock is a mixture of a plurality of feedstocks having alkene and alkane, e.g., at least one concentrated alkene feedstock having at least 80 mol. % alkene and at least one dilute alkene feedstock having 10-80 mol. % alkene.

In one embodiment, a plurality of feedstocks having alkene may be pre-mixed before being brought to the suitable conditions for alkylation reaction. In another embodiment of the invention, a plurality of feedstocks having alkene may be separately conditioned to the suitable conditions before feeding to the reaction zone(s). The relative amount of each separately conditioned alkene feedstock to be mixed and fed to the reaction zone(s) is varied based on the reaction conditions, catalyst (activity and amount), and space hour velocity. In one embodiment, the first few reaction zones of the reactor are fed with a second feedstock having higher alkene content than that of the second feedstock for the last few reaction zones.

Alkylation and Transalkylation Reactions

The process of this invention comprises feeding a predominantly liquid phase first feedstock and a vapor phase second feedstock to an alkylation reaction zone, the inlet portion operated under conditions to maintain the mixture of feedstocks in mixed phase. As used herein, the term "mixed phase" means partially liquid and partially vapor. The mixture further contacts an alkylation catalyst in the reaction zone to produce a first effluent stream. The first effluent stream exits the reaction zone in a predominantly liquid phase. The first effluent stream comprises the monoalkylated aromatic product, unreacted alkylatable aromatic compound, unreacted alkene, unreacted alkane, and polyalkylated aromatic compounds. The unreacted alkene and unreacted alkane are dissolved in the monoalkylated aromatic product, unreacted alkylatable aromatic compound, and polyalkylated aromatic compounds under the conditions at the exit of the reaction zone.

The phase change from mixed to liquid occurs in the catalyst bed due to conversion of the vapor-phase olefin to liquid-phase reaction products (mono- and di-alkylated aromatics). The present invention holds an advantage over the prior art in that allowing a mixed phase to be present at the inlet or any portion of the catalyst bed (or reaction zone) allows lower operating pressures which do not require expensive compressors to be installed. At the same time, designing the process such that a liquid phase exists at the outlet of the catalyst bed allows the achievement of high olefin conversion since olefin conversion is higher in the liquid phase than in a mixed phase environment.

|  | Liquid phase | Mixed Phase | Present Invention |
|---|---|---|---|
| Olefin Conversion | High | Moderate | High |
| Operating Pressure | High | Moderate | Moderate |

The conditions, i.e., temperature and pressure, together with the compositions of the first feedstock and the second feedstock control the phase of the mixture of the first feedstock and the second feedstock. Typically, liquid phase mixture is formed under lower temperature and higher pressure, and vapor phase mixture is formed under higher temperature and lower pressure. Under certain conditions, typically a range of temperature and pressure, a mixed phase (partially vapor and partially liquid) mixture can be formed. The compositions of the first feedstock and the second feedstock are also important parameters. Feedstocks with high content of low molecular weight molecule, e.g., methane and/or hydrogen, need higher pressure and lower temperature to maintain the mixture in liquid phase in comparison with the same feedstock with lower content of low molecular weight molecules. When a mixed phase is present, the lower molecular weight compounds (such as methane, ethylene and ethane) tend to preferentially comprise the vapor phase while high molecular weight components (such as benzene and mono- and poly-alkylated benzenes) tend to preferentially comprise the liquid phase.

In one embodiment, the conditions of the alkylation reaction zone, particularly the inlet portion of the reaction zone, include a temperature of 100 to 260° C. (212 to 500° F.) and a pressure of 689 to 4601 kPa-a (100 to 667 psia), preferably, a pressure of 1500 to 3500 kPa-a (218 to 508 psia). The conditions are such that only a portion of the alkene and alkane in the second feedstock is dissolved in the alkylatable aromatic compound in the first feedstock after mixing the first feedstock and the second feedstock at the inlet zone of the reaction zone. The mixture is in a mixed (vapor/liquid) phase.

The conditions of the downstream portion of the alkylation reaction zone include a temperature of 150 to 285° C. (302 to 545° F.) and a pressure of 689 to 4601 kPa-a (100 to 667 psia), preferably, a pressure of 1500 to 3000 kPa-a (218 to 435 psia), a WHSV based on alkene for overall reactor of 0.1 to 10 $h^{-1}$, preferably, 0.2 to 2 $h^{-1}$, more preferably, 0.5 to 1 $h^{-1}$, or a WHSV based on both alkene and benzene for overall reactor of 10 to 100 $h^{-1}$, preferably, 20 to 50 $h^{-1}$. Typically temperature is higher in the downstream portion of the reaction zone than the inlet portion of the reaction zone due to the exothermic nature of the alkylation reaction. The alkylatable aromatic compound is alkylated with the alkene in the second feedstock in the presence of an alkylation catalyst in a reactor having at least one reaction zone. The reaction zones are typically located in a single reactor vessel, but may include a reaction zone located in separate vessel which may be a by-passable and which may operate as a reactive guard bed. The reaction zone may include an alkylation catalyst bed or multiple alkylation catalyst beds. The catalyst composition used in the reactive guard bed may be different from the catalyst composition used in the alkylation reactor. The catalyst composition used in the reactive guard bed may have multiple catalyst compositions. At least the first alkylation reaction zone, and normally each alkylation reaction zone, is operated under conditions effective to cause alkylation of the alkylatable aromatic compound with the alkene component of the second feedstock in the presence of a alkylation catalyst.

The effluent from the first alkylation reaction zone (first product) comprises the desired monoalkylated aromatic product, unreacted alkylatable aromatic compound, any unreacted alkene (alkene conversion is expected to be at least 90 mol. %, preferably, above 98 mol. %) and the alkane component and the other impurities. The temperature, pressure, and composition of the effluent is such that the effluent is maintained in liquid phase predominantly liquid phase which is substantially free of vapor when the effluent exits the reaction zone. The temperature of the effluent is typically higher than the temperature of the feed because the alkylation reaction is generally exothermic. To maintain the reaction zone in mixed-phase/liquid-phase and the effluent exiting the reaction zone in liquid phase, the effluent is typically removed from the first reaction zone and cooled before entering the second reaction zone. The effluent can also be cooled by internal cooling system between reaction zones. At least a portion of the effluent is fed to the second alkylation reaction zone where additional second feedstock is added for reaction with the unreacted alkylatable aromatic compound with a second catalyst. Where the process employs a reactor with more than two alkylation reaction zones, the effluent from each zone is fed to the next zone with additional second feedstock. Furthermore, at least a portion the effluent from the last alkylation reaction zone and/or other zones can be fed directly or indirectly to a transalkylation unit.

The term "predominately liquid phase" used herein is to be understood that the feedstock or the effluent has at least 95 wt. % of liquid phase, preferably, at least 98 wt. % liquid phase, even preferably, at least 99 wt. % liquid phase, more preferably, at least 99.5 wt. % liquid phase.

In addition to, and upstream of, the operatively connected alkylation zones, the alkylation reaction system may also include a by-passable reactive guard bed normally located in a pre-reactor separate from the remainder of the alkylation reactor. The reactive guard bed may also loaded with alkylation catalyst, which may be the same or different from the catalyst used in the multi-stage alkylation reaction system. The reactive guard bed is maintained from under ambient or up to alkylation conditions. At least a portion of alkylatable aromatic compound and typically at least a portion of the second feedstock are passed through the reactive guard bed prior to entry into the first reaction zone of the operatively connected alkylation reaction zones in the reactor. The reactive guard bed not only serves to affect the desired alkylation reaction but is also used to remove any reactive impurities in the feeds, such as nitrogen compounds, which could otherwise poison the remainder of the alkylation catalyst. The catalyst in the reactive guard bed is therefore subject to more frequent regeneration and/or replacement than the remainder of the alkylation catalyst and hence the guard bed is normally provided with a by-pass circuit so that the alkylation feedstock can be fed directly to the series connected alkylation reaction zones in the reactor when the guard bed is out of service. The reactive guard bed may operate in the all liquid phase or in a mixed-phase in co-current upflow or downflow operation.

The alkylation reactor used in the process of the present invention is normally operated so as to achieve essentially complete conversion of the alkene in the second feedstock. However, for some applications, it may be desirable to operate at below 100% alkene conversion. The employment a separate finishing reactor downstream of the multi-zones alkylation reactor may be desirable under certain conditions. The finishing reactor would also contain alkylation catalyst, which could be the same or different from the catalyst used in the alkylation reactor and could be operated under liquid, mixed or vapor phase alkylation conditions.

The alkylation reactor used in the process of the present invention is highly selective to the desired monoalkylated product, such as ethylbenzene, but normally produces at least some polyalkylated species. Thus the effluent from the final alkylation reaction zone is supplied to a transalkylation reactor which is normally separate from the alkylation reactor. The transalkylation reactor produces additional monoalkylated product by reacting the polyalkylated species with additional aromatic compound.

Particular conditions for carrying out the mix-phase to liquid-phase alkylation of benzene with ethylene may include a temperature of from about 120 to 285° C., preferably, a temperature of from about 150 to 260° C., a pressure of 689 to 4601 kPa-a (100 to 667 psia), preferably, a pressure of 1500 to 3000 kPa-a (218 to 435 psia), a WHSV based on ethylene for overall reactor of 0.1 to 10 $h^{-1}$, preferably, 0.2 to 2 $h^{-1}$, more preferably, 0.5 to 1 $h^{-1}$, or a WHSV based on both ethylene and benzene for overall reactor of 10 to 100 $h^{-1}$, preferably, 20 to 50 $h^{-1}$, and a mole ratio of benzene to ethylene from about 1 to about 10.

Where the alkylation system includes a reactive guard bed, it is operated under at least partial liquid phase conditions. The guard bed will preferably operate at a temperature of from about 120 to 285° C., preferably, a temperature of from about 150 to 260° C., a pressure of 689 to 4601 kPa-a (100 to 667 psia), preferably, a pressure of 1500 to 3000 kPa-a (218 to 435 psia), a WHSV based on ethylene for overall reactor of 0.1 to 10 $h^{-1}$, preferably, 0.2 to 2 $h^{-1}$, more preferably, 0.5 to 1 $h^{-1}$, or a WHSV based on both ethylene and benzene for overall reactor of 10 to 100 $h^{-1}$, preferably, 20 to 50 $h^{-1}$, and a mole ratio of benzene to ethylene from about 1 to about 10.

The polyalkylated aromatic compounds in the effluents may be separated for transalkylation with alkylatable aromatic compound(s). Monoalkylated aromatic compound is made by transalkylation between polyalkylated aromatic compounds and the alkylatable aromatic compound.

In one embodiment, the transalkylation reaction takes place under liquid phase conditions. Particular conditions for carrying out the liquid phase transalkylation of polyethylbenzene(s) with benzene may include a temperature of from about 150° to about 260° C., a pressure of 696 to 4137 kPa-a (101 to 600 psia), a WHSV based on the weight of the polyethylbenzene(s) feed to the reaction zone of from about 0.5 to about 100 $hr^{-1}$ and a mole ratio of benzene to polyethylbenzene(s) of from 1:1 to 30:1, preferably, 1:1 to 10:1, more preferably, 1:1 to 5:1.

In another embodiment, the transalkylation reaction takes place under vapor phase conditions. Particular conditions for carrying out the vapor phase transalkylation of polyethylbenzenes with benzene may include a temperature of from about 350 to about 450° C., a pressure of 696 to 1601 kPa-a (101 to 232 psia), a WHSV based on the weight of the polyethylbenzene(s) feed to the reaction zone of from about 0.5 to about 20 $hr^{-1}$, preferably, from about 1 to about 10 $hr^{-1}$, and a mole ratio of benzene to polyethylbenzene(s) of from 1:1 to 5:1, preferably, 2:1 to 3:1.

In yet another embodiment of this invention, the process may be used by retrofitting existing ethylbenzene or cumene plants with minimum modification. The existing ethylbenzene or cumene process may be a vapor phase, liquid phase, or mixed phase alkylation reactor.

Catalysts

Suitable alkylation and transalkylation catalyst used in the present invention is comprised of a molecular sieve that includes, but is not limited to MCM-22, MCM-49, MCM-36, MCM-56, beta zeolite, faujasite, mordenite, PSH-3, SSZ-25, ERB-1, ITQ-1, ITQ-2. MCM-22 and its use to catalyze the synthesis of alkylaromatics, including ethylbenzene, are described in U.S. Pat. Nos. 4,992,606; 5,077,445; and 5,334,795. PSH-3 is described in U.S. Pat. No. 4,439,409. SSZ-25 and its use in aromatic alkylation are described in U.S. Pat. No. 5,149,894. ERB-1 is described in European Patent No. 0293032. ITQ-1 is described in U.S. Pat. No. 6,077,498. ITQ-2 is described in International Patent Publication No. WO97/17290 and WO01/21562. MCM-36 is described in U.S. Pat. Nos. 5,250,277 and 5,292,698. U.S. Pat. No. 5,258,565 describes the synthesis of alkylaromatics, including ethylbenzene, using a catalyst comprising MCM-36. MCM-49 is described in U.S. Pat. No. 5,236,575. The use of MCM-49 to catalyze the synthesis of alkylaromatics, including ethylbenzene, is described in U.S. Pat. Nos. 5,493,065 and 5,371,310. MCM-56 is described in U.S. Pat. No. 5,362,697. The use of MCM-56 to catalyze the synthesis of alkylaromatics including ethylbenzene is described in U.S. Pat. Nos. 5,557,024 and 5,453,554. The entire contents of all the above patent specifications are incorporated herein by reference.

Alternatively, the alkylation and transalkylation catalyst of the present invention may comprise a medium pore molecular sieve having a Constraint Index of 2-12 (as defined in U.S. Pat. No. 4,016,218), including ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. The entire contents of all the above patent specifications are incorporated herein by reference.

As a further alternative, the alkylation and transalkylation catalyst can comprise a large pore molecular sieve having a Constraint Index less than 2. Suitable large pore molecular sieves include zeolite beta, zeolite Y, Ultrastable Y (USY), Dealuminized Y (Deal Y), rare earth exchanged Y (REY), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. Nos. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. The entire contents of all the above patent specifications are incorporated herein by reference.

The same catalyst may be used in both the transalkylation zone and the alkylation zones of the present invention. Preferably, however, catalysts are chosen for the different alkylation zones and the transalkylation zone, so as to be tailored for the particular reactions catalyzed therein. In one embodiment of the present invention, a standard activity catalyst for example, 50% zeolite and 50% binder is used in the higher temperature alkylation catalyst beds and a higher activity catalyst for example, 75% zeolite and 25% binder is used in the lower temperature alkylation catalyst beds, while suitable transalkylation catalyst is used in the transalkylation zone. In such an embodiment, any finishing reactor zone could include a MCM-22 catalyst bed for liquid phase operation.

In the process of the invention, the alkylation reaction in at least the first, and normally in each, of the operatively connected alkylation reaction zones takes place under liquid phase conditions, such that the alkylatable aromatic compound is in the liquid phase. The invention will be more particularly described with reference to the following Examples

EXAMPLE 1

Liquid Phase Alkylation

The following example is a computer simulation of benzene ethylation with ethylene in liquid phase. Simulation results were obtained using a proprietary numerical software package. Vapor-liquid equilibrium was calculated, the Soave-Redlich-Kwong Equation-of-State (with optimized interaction coefficients).

The feed to each catalyst bed is characterized by a B/E ratio (Benzene to Ethylene molar ratio) and an E/E ratio (Ethylene to Ethane molar ratio). The very high E/E ratio is an indication of an ethylene feedstock with a chemical or polymer grade ethylene purity. The liquid phase alkylation is configured to operate in the liquid phase. The temperatures and pressures of the feed and effluent streams to each bed are sufficient to allow all liquid phase operation in the catalyst bed. The results of the simulation are shown in Table 1.

TABLE 1

| | | Ethylene Conversion (%) | EB cumulative yield (mol. %) | B/E ratio | E/E ratio | Fraction Liquid | Temperature (° C.) | Pressure (kPa-a) |
|---|---|---|---|---|---|---|---|---|
| Bed 1 | Feed | — | | 21.0 | 261 | 1 | 222.2 | 4270 |
| | Effluent | 100 | 4.8 | — | — | 1 | 246.3 | 4220 |
| Bed 2 | Feed | — | | 20.0 | 229 | 1 | 242.6 | 4210 |
| | Effluent | 100 | 9.0 | — | — | 1 | 265 | 4165 |
| Bed 3 | Feed | — | | 19.1 | 203 | 1 | 222.9 | 4035 |
| | Effluent | 100 | 13.0 | — | — | 1 | 246.4 | 3980 |
| Bed 4 | Feed | — | | 18.1 | 183 | 1 | 242.9 | 3980 |
| | Effluent | 100 | 16.9 | — | — | 1 | 264.9 | 3915 |
| Bed 5 | Feed | — | | 17.2 | 166 | 1 | 223.5 | 3715 |
| | Effluent | 100 | 20.6 | — | — | 1 | 246.4 | 3660 |
| Bed 6 | Feed | — | | 16.3 | 152 | 1 | 243.1 | 3660 |
| | Effluent | 100 | 24.1 | — | — | 1 | 264.7 | 3590 |

EXAMPLE 2

Mixed-Phase/Liquid-Phase Design

The following example is a computer simulation of mixed-phase/liquid-phase benzene ethylation with ethylene by the process of the present invention. The case is configured to operate in mixed-phase/liquid-phase. The temperatures and pressures of the feed and effluent streams to each bed are sufficient to allow mixed-phase/liquid-phase operation in the catalyst bed. The results of the simulation are shown in Table 2. Note that pressure increases across bed 1 (the RGB) due to downflow operation.

TABLE 2

| | | Ethylene Conversion (%) | EB cumulative yield (mol. %) | B/E ratio | E/E ratio | Fraction Liquid | Temperature (° C.) | Pressure (kPa-a) |
|---|---|---|---|---|---|---|---|---|
| Bed 1 | Feed | — | — | 20.0 | 48.8 | 1 | 170 | 3330 |
| | Effluent | 100 | 5.1 | — | — | 1 | 241.7 | 3380 |
| Bed 2 | Feed | — | — | 6.1 | 48.8 | 0.93 | 170 | 3160 |
| | Effluent | 100 | 17.6 | — | — | 1 | 250 | 3150 |
| Bed 3 | Feed | — | — | 5.4 | 48.8 | 0.93 | 170 | 3050 |
| | Effluent | 100 | 28.2 | — | — | 1 | 245 | 3040 |
| Bed 4 | Feed | — | — | 4.7 | 48.8 | 0.93 | 170 | 2940 |
| | Effluent | 100 | 37.2 | — | — | 1 | 239.9 | 2930 |

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. A process for producing an alkylated aromatic product which comprises ethylbenzene or cumene in a first reaction zone of an alkylation reactor, comprising the steps of:
   (a) co-currently feeding a predominantly liquid phase first feedstock which comprises benzene and an at least partially vapor phase second feedstock which comprises at least one alkene compound selected from the group consisting of ethylene and propylene and at least one alkane compound selected from the group consisting of methane, ethane, and propane, to an inlet portion of said first reaction zone, wherein said first reaction zone is operated under conditions sufficient to ensure that the mixture of said first feedstock and said second feedstock is in mixed phase in at least a portion of said reaction zone; and
   (b) contacting said feedstock mixture and a first alkylation catalyst which comprises a molecular sieve selected from the group consisting of MCM-22, MCM-36, MCM-49 and MCM-56, beta zeolite, faujasite, mordenite, PSH-3, SSZ-25, ERB-1, ITQ-1, ITQ-2, zeolite Y, Ultrastable Y (USY), Dealuminized Y (DealY), rare earth exchanged Y (REY), ZSM-3, ZSM-4, ZSM-18, ZSM-20, and any combination thereof, in said first reaction zone, to produce a first effluent which comprises said alkylated aromatic product and polyalkylated aromatic compounds, wherein said first effluent exits said reaction zone in at least 95 wt. % liquid phase in the presence of said alkane, downstream of said inlet portion of said reaction zone; and
   wherein said conditions of said reaction zone are sufficient to ensure a phase change from mixed phase to liquid phase in at least a portion of said first reaction zone.

2. The process of claim 1, wherein said conditions of said inlet portion of said first reaction zone include a temperature of 120 to 260° C. and a pressure of 689 to 4601 kPa-a (100 to 667 psia), a WHSV based on the weight of alkene of 0.1 to 10 $h^{-1}$.

3. The process of claim 1, wherein said first feedstock has at least 98 wt. % liquid phase.

4. The process of claim 1, wherein said second feedstock comprises at least 50 mol. % alkene.

5. The process of claim 1, further comprising the step of:
   (c) contacting said polyalkylated aromatic compounds and a third feedstock which comprises alkylatable aromatic compound(s) in the presence of a transalkylation catalyst in a transalkylation reaction zone under transalkylation conditions, to produce a transalkylation effluent which comprises additional monoalkylated aromatic product.

6. The process of claim 5, further comprising the step of:
   (d) separating said first and/or transalkylation effluents to recover said monoalkylated aromatic product.

7. The process of claim 5, wherein said transalkylation catalyst comprises a molecular sieve selected from the group consisting of MCM-22, MCM-36, MCM-49 and MCM-56, beta zeolite, faujasite, mordenite, PSH-3, SSZ-25, ERB-1, ITQ-1, ITQ-2, zeolite Y, Ultrastable Y (USY), Dealuminized Y (DealY), rare earth exchanged Y (REY), ZSM-3, ZSM-4, ZSM-18, ZSM-20, and any combination thereof.

8. The process of claim 5, wherein said transalkylation conditions are effective to maintain said transalkylation effluent stream substantially in a vapor phase.

9. The process of claim 5, wherein said transalkylation conditions are effective to maintain said transalkylation effluent stream substantially in a liquid phase.

10. The process of claim 8, wherein said vapor phase transalkylation conditions include a temperature of 350 to 450° C. and a pressure of 696 to 1601 kPa-a (101 to 232 psia), a WHSV based on the weight of said polyalkylated aromatic compounds of about 0.5 to 20 $h^{-1}$, a mole ratio of said alkylatable aromatic compound to said polyalkylated aromatic compounds of 1:1 to 5:1.

11. The process of claim 9, wherein said liquid phase transalkylation conditions include a temperature of 150 to 260° C. and a pressure of 696 to 4137 kPa-a (101 to 600 psia), a WHSV based on the weight of said polyalkylated aromatic compounds of about 0.5 to 100 $h^{-1}$, a mole ratio of said alkylatable aromatic compound to said polyalkylated aromatic compounds of 1:1 to 10:1.

12. The process of claim 5, further comprising the steps of:
   (d) cooling said first effluent stream to form a cooled first effluent stream;
   (e) feeding a mixture of at least a portion of said cooled first effluent stream and additional second feedstock to a second reaction zone of said alkylation reactor operated under second conditions; and
   (f) contacting the mixture of step (e) with a second alkylation catalyst in said second reaction zone to produce a second effluent which comprises additional monoalkylated aromatic product.

13. The process of claim 12, wherein said second conditions are effective to maintain said mixture of step (e) in a mixed phase.

14. The process of claim 13, wherein said second conditions include a temperature of 120 to 285° C. and a pressure of 689 to 4601 kPa-a (100 to 667 psia), a WHSV based on the weight of alkene of 0.1 to 10 $h^{-1}$.

15. The process of claim 12, wherein said second conditions are effective to maintain said mixture of step (e) in a liquid phase.

16. The process of claim 12, wherein said second alkylation catalyst comprise a molecular sieve selected from the group consisting of MCM-22, MCM-36, MCM-49 and MCM-56, beta zeolite, faujasite, mordenite, PSH-3, SSZ-25, ERB-1, ITQ-1, ITQ-2, zeolite Y, Ultrastable Y (USY), Dealuminized Y, rare earth exchanged Y (REY), ZSM-3, ZSM-4, ZSM-18, ZSM-20, and any combination thereof.

17. The process of claim 12, further comprising the step of:
   (g) separating said first and second effluents, to recover said monoalkylated aromatic product.

18. The process of claim 17, further comprising the steps of:
(h) further separating from said first and second effluents said polyalkylated aromatic compounds as a transalkylation feedstock; and
(i) contacting said transalkylation feedstock with said third feedstock which comprises said alkylatable aromatic compounds in the presence of a transalkylation catalyst in a transalkylation reaction zone under transalkylation conditions, to produce a third effluent which comprises additional monoalkylated aromatic product.

19. The process of claim 18, further comprising the step of:
(j) separating said third effluent, to recover said additional monoalkylated aromatic product.

20. The process of claim 18, wherein said transalkylation catalyst comprises a molecular sieve selected from the group consisting of MCM-22, MCM-36, MCM-49 and MCM-56, beta zeolite, faujasite, mordenite, PSH-3, SSZ-25, ERB-1, ITQ-1, ITQ-2, zeolite Y, Ultrastable Y (USY), Dealuminized Y, rare earth exchanged Y (REY), ZSM-3, ZSM-4, ZSM-18, ZSM-20, and any combination thereof.

21. A process for producing a monoalkylated aromatic product as recited in claim 1, where said process is applied to retrofitting an existing ethylbenzene or cumene plant and further comprises the steps of:
(c) cooling said first effluent stream to form a cooled first effluent stream; and
(d) feeding a mixture of at least a portion of said cooled first effluent stream and additional second feedstock to a second reaction zone of said multistage reactor operated under second conditions.

22. The process of claim 21, further comprising the step of:
(e) contacting the mixture of step (d) with a transalkylation catalyst in said second reaction zone to produce a transalkylation effluent which comprises additional monoalkylated aromatic product.

23. The process of claim 22, wherein said transalkylation catalyst comprises a molecular sieve selected from the group consisting of beta zeolite, faujasite, mordenite, zeolite Y, Ultrastable Y (USY), Dealuminized Y (DealY), rare earth exchanged Y (REY), and any combination thereof.

* * * * *